United States Patent [19]

Gaston-Johansson

[11] Patent Number: 5,692,500

[45] Date of Patent: Dec. 2, 1997

[54] PAIN MEASUREMENT AND RECORDING TOOL AND METHOD

[76] Inventor: Fannie Gaston-Johansson, 5884 Pimlico Rd., Baltimore, Md. 21209

[21] Appl. No.: 369,770

[22] Filed: Jan. 9, 1995

[51] Int. Cl.$^6$ ................................................. A61B 5/00
[52] U.S. Cl. ................................... 128/630; 128/897
[58] Field of Search .................... 128/897–98, 630, 128/744

[56] References Cited

U.S. PATENT DOCUMENTS

| | | | |
|---|---|---|---|
| 4,844,091 | 7/1989 | Bellak | 128/744 |
| 5,018,526 | 5/1991 | Gaston-Johannson | 128/630 |

FOREIGN PATENT DOCUMENTS

| | | | |
|---|---|---|---|
| 0858781 | 8/1981 | U.S.S.R. | 128/630 |

*Primary Examiner*—John P. Lacyk
*Attorney, Agent, or Firm*—John A. Beehner

[57] ABSTRACT

A tool for providing a multidimensional indication of the pain being experienced by a person includes multiple sets of selection indicators and sliding scales, each being indicative of variations of a respective dimension of pain selected from the group consisting of nature, intensity, location, duration, continuity and pain relief. The selection indicators are mounted on the tool in association with pain descriptors, i.e. words, with the selection indicators being adjustable between first and second states indicating whether the associated descriptor describes their pain. Likewise, the slidable scale indicators are adjustable along each of the pain scales to indicate the relative degree of the respective dimension of pain that most closely represents the pain they are experiencing. Finally, the tool displays illustrations of a human body in association with a grid for identifying the location of pain being experienced by the user. The method of the invention includes the steps of providing such a tool, causing a person to adjust the selection indicators and scale indicators to the appropriate positions for accurately describing their pain and observing those indications of pain recorded on the tool.

30 Claims, 5 Drawing Sheets

PAIN MEASUREMENT AND RECORDING TOOL AND METHOD

BACKGROUND OF THE INVENTION

The present invention is directed generally to a tool for providing a multidimensional indication of the pain being experienced by a person, and more particularly to a handheld tool having indicators thereon which may be adjusted by a person to provide a reliable and physical indication of the type and intensity of pain being experienced by the person, as well as the location, duration and continuity of the pain and level of pain relief experienced.

Pain is the number one complaint of all patients consulting a physician. It is estimated that 50–75 million Americans suffer from some type of pain and approximately 40 billion dollars are spent annually on the treatment of pain. Given the magnitude and significance of the problem, it is surprising to find that there is no pain tool being systematically used in hospitals to assess the intensity, quality, location, and duration of a patient's pain. Appropriate assessment of a patient's pain is a prerequisite to successful diagnosis and treatment of the pain.

Health care professionals have an ethical obligation to adequately assess and manage pain in order to relieve the patients' suffering. Findings from research studies over the past 20 years have been consistent in showing that patients suffering from pain are under medicated up to 50% of the time by nurses. These findings are further compounded by the fact that research studies have shown that physicians underprescribed pain medication by an additional 50%.

Several research studies have shown that health professionals do not always see the situation as patients see it. The general trend seems to be that nurses and physicians infer less pain than patients say they experience. The importance of pain assessment and management is further increased when additional benefits such as earlier mobilization, shorter hospital stay, and reduced cost are realized.

In order to come to grips with the problem of inadequate pain assessment and pain management in health care facilities, standards of care and guidelines have been developed by the American Pain Society and experts in pain management. Standards and guidelines are statements that define the quality of care that patients can expect from a health care facility. The following statements clearly support the use of a simple, valid and reliable pain tool, used by health professions, to assess a patient's pain.

"The intensity of pain is assessed a documented on admission after any know pain producing procedure, with each new report of pain and routinely at regular intervals depending on the severity of the patient's pain. A simple, valid measure of pain intensity will be selected by each clinical unit" (Standard by American Pain Society 1990).

"Pain assessment and reassessment are prerequisites to effective pain control. Simple and reliable pain assessment tools should be used routinely to monitor the patient's pain. The word simple is used to refer to a pain. tool that provides a multidimensional assessment of pain and is easily understood and completed by patients within a few minutes" (Pain Guidelines: Department of Health and Human Services, 1992).

When a person in need of medical treatment first contacts a doctor or a nurse, the person generally attempts to verbally describe his or her pain so that the medical personnel can make at least an initial diagnosis of the patient's condition and plan the appropriate treatment. This presents a significant problem for medical personnel, however, due to the fact that different people experience and, therefore, describe their pain or symptoms in different ways. One person may be stronger than another. A third person may have become accustomed to the ache after a period of time and, therefore, may describe the ache with milder words than he would have used if the ache had recently occurred. The changing expressions for pain which a diagnostician may hear complicates the quick and definite diagnosis of a person's illness or injury.

Devices for measuring pain have previously been proposed, such as that disclosed in United Kingdom Patent Application GB 2 049 431 A, which provides a sliding scale displaying a straight line with "no pain" indicated at one end and "intense pain" indicated at the other end of the line and an indicator slidable on the scale by a person to the position which corresponds proportionately to the pain felt by the person. But this device suffers from the same shortcoming as verbal communication in that it measures pain in only one dimension and based on the person's own very subjective assessment of what he feels.

This inventor's own U.S. Pat. No. 5,018,526 discloses a tool which has been successfully used to enable patients to more effectively and accurately communicate the nature and intensity of pain they have experienced but that device was not intended to measure or record further dimensions of pain such as location on the body, duration or continuity of the pain and the level of any pain relief experienced by the patient.

Accordingly, there is a need for a simple device for providing a reliable assessment of the pain experienced by a person so that an accurate diagnosis may be made and early treatment begun.

A primary object of the invention, therefore, is to provide a simple yet effective tool for providing a reliable multidimensional indication of the pain being experienced by a person.

Another object is to provide such a tool which is readily adjusted by a person to record the pain experienced by him or her at that time.

Another object is to provide such a tool which assists patients to effectively communicate information describing the various dimensions of their pain.

Another object is to provide such a tool which provides physical indicators of the pain experienced by a person so that its use does not require the assistance of another person to separately record the information and so that the indicated pain reading is preserved until the instrument is altered, reset or reused.

Another object is to provide such a tool which affords the patient a visual indication of relative degrees of pain, yet simultaneously affords medical personnel or the person a definite quantitative measurement of the level of pain indicated by the person.

Another object is to provide such a tool which records information indicative of the location of pain experienced by a person.

Another object is to provide such a tool which records information indicative of the duration of pain experienced by a person.

Another object is to provide such a tool which records information indicative of the continuity of pain experienced by a person, i.e., whether it is continuous or whether it comes and goes.

Another object is to provide such a tool with an indicator of the level of pain relief experienced by a person.

3

Another object is to provide such a tool which is simple and rugged in construction, inexpensive to manufacture and efficient in operation.

SUMMARY OF THE INVENTION

An instrument for providing a multidimensional indication of the pain being experienced by a person includes an elongated base having a series of selection indicators and slide scales, each indicative of variations of a respective dimension of pain selected from the group consisting of nature, intensity, location, duration, continuity and pain relief. Each selection indicator is adjustable by a person between a first state indicating that the associated descriptor describes the person's pain and a second state indicating that the associated descriptor does not describe the person's pain. Accordingly, a person need only adjust each sensor to the appropriate first or second state to afford a ready indication of whether the associated descriptor is descriptive of their pain.

The tool is furthermore provided with a first elongated pain scale providing visible indicia symbolizing the range of another dimension of pain selected from the above mentioned group. A first scale indicator is slidable on the base to a selected position along the scale to provide a cognitive measurement of the respective dimension of pain being experienced by the person. A second scale may be provided on the base, preferably out of view of the first elongated pain scale, but at a position for cooperation with the first scale indicator to provide a quantitative reading which is indicative of the adjusted position of the scale indicator on the first elongated pain scale.

The tool may be provided with another set of selection indicators indicative of variations in a still further dimension of pain selected from the above mentioned group and one or more additional scales and scale indicators may be provided on the body of the tool for recording and indicating variations in still further dimensions of pain. The preferred instrument would include either selection indicators or scales for indicating variations in all of the following dimensions of pain, namely nature, intensity, location, duration, continuity and pain relief.

In accordance with the method of the invention, such a tool is handed to a person who has been requested to adjust the various selection indicators to indicate whether the associated pain descriptor accurately describes the pain that they feel. Similarly, the person is requested to adjust each sliding scale indicator to the position which most appropriately indicates the relative degree of the respective dimension of pain being experienced by the person. The adjusted tool can then be examined immediately or at any later time to afford a multidimensional indication of the pain experienced by the person at the time the tool was used.

A particular advantage is that use of the tool does not require a second person to be present to record descriptors or scale settings selected by the person, since the instrument itself affords the physical indicators for recording right on the instrument, which descriptors and scale settings are selected. This eliminates the possibility of human errors in recording the information and also affords a way of preserving the person's selections for later review, observation or recording.

The pain measurement and recording tool and method of the invention thus help patients to more effectively communicate pain. This assists health professionals to interpret pain, diagnose diseases and select appropriate treatment. Repetitive use of the tool over time assists in evaluating the efficacy of pain treatment.

4

DESCRIPTION OF THE PREFERRED EMBODIMENT

Figure 1:
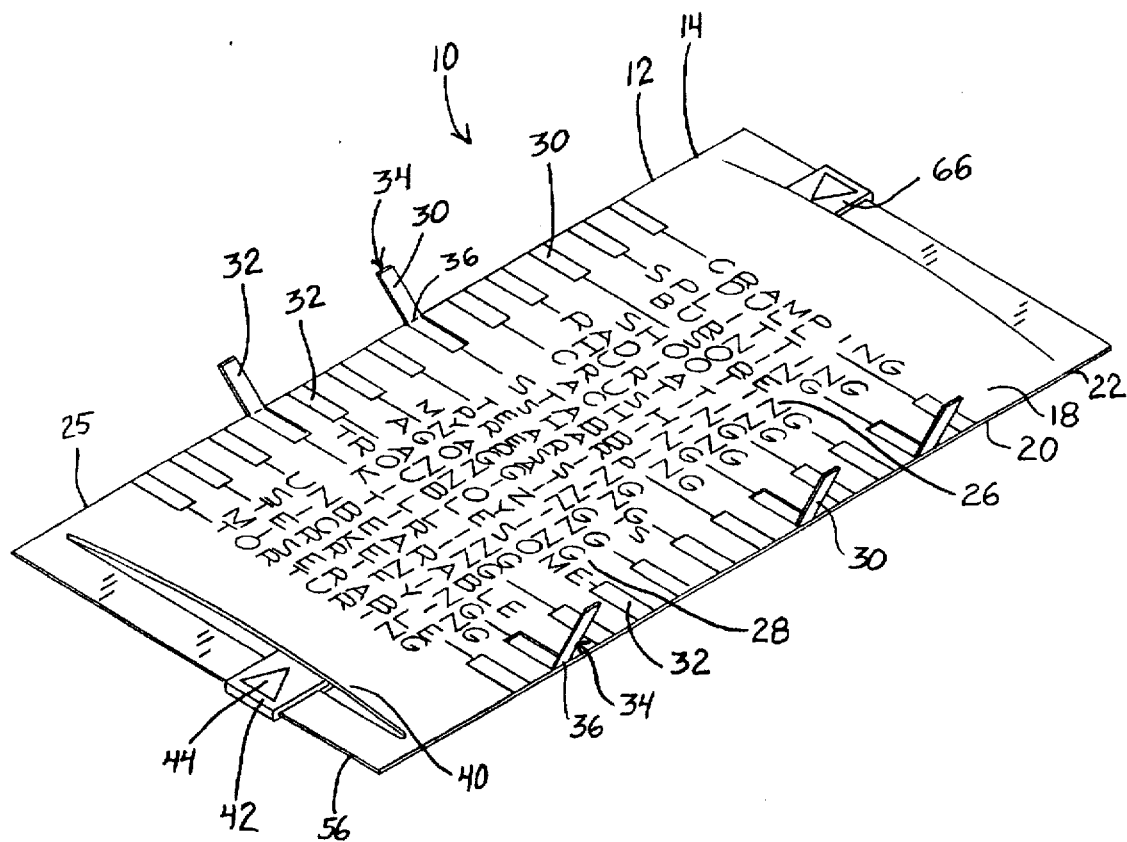
FIG. 1 is a perspective view of the pain measurement and recording tool of the invention.

The multidimensional pain measurement tool 10 of the invention is illustrated in the drawings as including an elongated base 12 on which various indicators are provided to give measurements of variations of respective dimensions of pain such as the nature, intensity, location, duration, continuity and pain relief as explained in further detail below.

Figure 4:
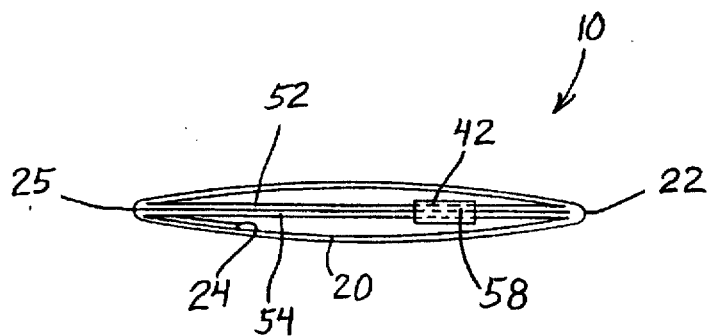
FIG. 4 is an end view of the pain measurement and recording tool.
Figure 6:
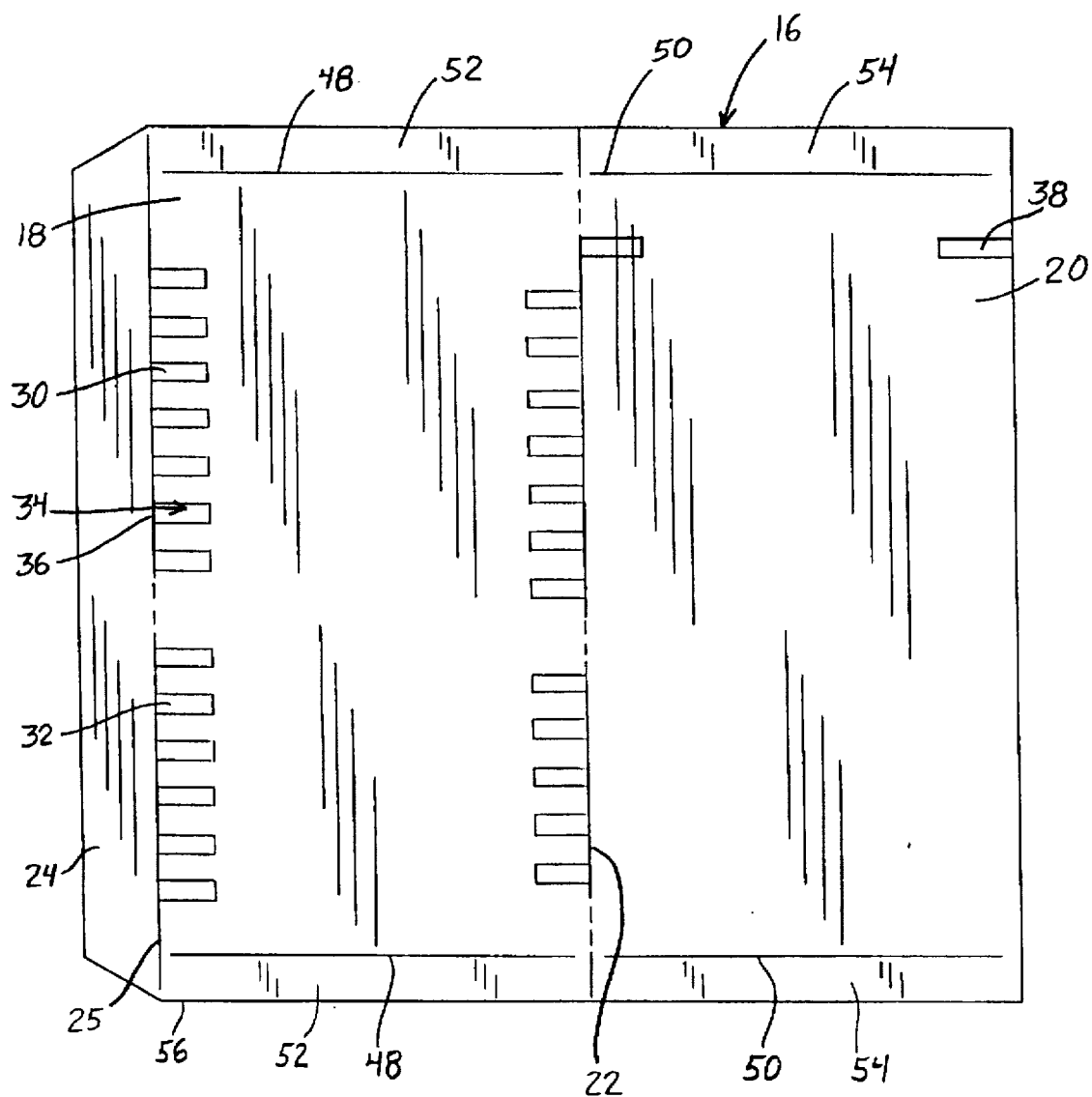
FIG. 6 is a plan view of the blank from which the tool is formed.

In the illustrated embodiment, base 12 is a flat sleeve 14 formed from the flat blank 16 as illustrated in FIG. 6. Blank 16 includes a top panel 18, a bottom panel 20 foldably connected to top panel 18 along side edge 22, and a securement flange 24 foldably connected to the opposite side edge 25 of top panel 18. In the bottom view of FIG. 4, it can be seen that the bottom panel 20 is folded under top panel 18 and secured by adhesives or the like to securement flange 24 to form the sleeve 14.

A first series of pain descriptors are printed or displayed on top surface 14 to describe the nature of pain experienced by a person. That first series includes a list of sensory pain descriptors 26 in column format on an upper portion of top surface 14 and generally centered between edges 18 and 20. The sensory pain descriptors 26 are words describing various degrees and characteristics of the sensory nature or dimension of experiencing pain. A numerical rank is assigned to each of the descriptors, as indicated in the following chart, but these rank numbers are not displayed on the instrument. The descriptors are preferably arranged in random order with respect to rank so that the order on the instrument does not correlate to the numerical rank. The purpose of the numerical rank is discussed hereinafter.

The first series of pain descriptor further includes a list of emotional pain descriptors 28 below the sensory pain descriptors 26 on top surface 14. These emotional pain descriptors are also set for the in the following chart with their assigned rank:

| | Rank |
|---|---|
| Sensory Pain Descriptor | |
| Cramping | 4 |
| Dull | 1 |
| Splitting | 5 |
| Burning | 4 |
| Searing | 4 |
| Sore | 1 |
| Shooting | 5 |

-continued

|              | Rank |
|--------------|------|
| Radiating    | 3    |
| Hurting      | 2    |
| Crushing     | 4    |
| Aching       | 3    |
| Stabbing     | 5    |
| Sharp        | 5    |
| Tearing      | 5    |
| Pressing     | 2    |
| Emotional Pain Descriptor | |
| Nagging      | 1    |
| Agonizing    | 4    |
| Annoying     | 1    |
| Troublesome  | 2    |
| Killing      | 5    |
| Tiring       | 3    |
| Unbearable   | 5    |
| Sickening    | 4    |
| Terrifying   | 5    |
| Miserable    | 3    |
| Torturing    | 5    |

The emotional pain descriptors 28 are words which define degrees or characteristics of the emotional nature of experiencing pain. Both the sensory pain descriptors 26 and emotional pain descriptors 28 were scientifically determined by research involving people with diverse backgrounds, i.e. African American, Whites, Native Americans, and Hispanics, as well as nurses, physicians and patients experiencing slight and chronic pain.

The numerical ranks assigned to the descriptors constitute a pain rating index with "1" indicative of least pain and "5" indicative of most pain. A total of the ranks of a person's choice of words descriptive of their pain is calculated to determine pain intensity.

Two major indexes are obtained for the emotional, as well as the sensory components of pain:

(a) The number of words chosen (NWC), and (b) The pain rating index rank (PRIR), based on a summation of the numerical values assigned to the chosen words. Subjects are asked to choose from each group of descriptors those words which best describe their pain. The quality of pain is reflected in the specific words chosen by the subjects, and pain intensity is calculated on the basis of the number of words chosen and the pain rating index rank. Thus, this instrument allows pain to be analyzed both quantitatively and qualitatively.

In order to physically indicate a person's choice of the first series of pain descriptors, base 12 includes a plurality of selection indicators 30 and 32 which are arranged in longitudinally spaced relation adjacent side edges 18 and 20 at positions aligned with and corresponding to the respective descriptors 26 and 28. Whereas the selection indicators may take many forms, the selection indicator 32 of the preferred embodiment is illustrated in FIG. 1 as a pivotal tab 34 formed in top panel 18 and having one end 36 pivotally connected to top panel 18 so that the tab is selectively adjustable between a substantially intact position within the plane of top panel 18 and a pivotally raised position engaging the top panel 18 only at the connected end 36 of tab 34. The tabs 34 may be die cut or otherwise perforated from the top panel 18 so that finger pressure from the underside of the tool will cause the tab to be slightly raised sufficiently to be engaged by fingernail for flipping it to the raised position.

All of the tabs 34 are thus pivotal between the intact and raised positions indicated in FIG. 1. The pivotally raised position preferably indicates a first state meaning that the associated descriptor accurately describes the person's pain. The intact position would then indicate a second state meaning that the associated descriptor does not describe the person's pain. The tool may preferably be handed to a person with all tabs 24 arranged in the intact position so that the person can raise only those tabs which accurately describe his or her pain.

Figure 3:
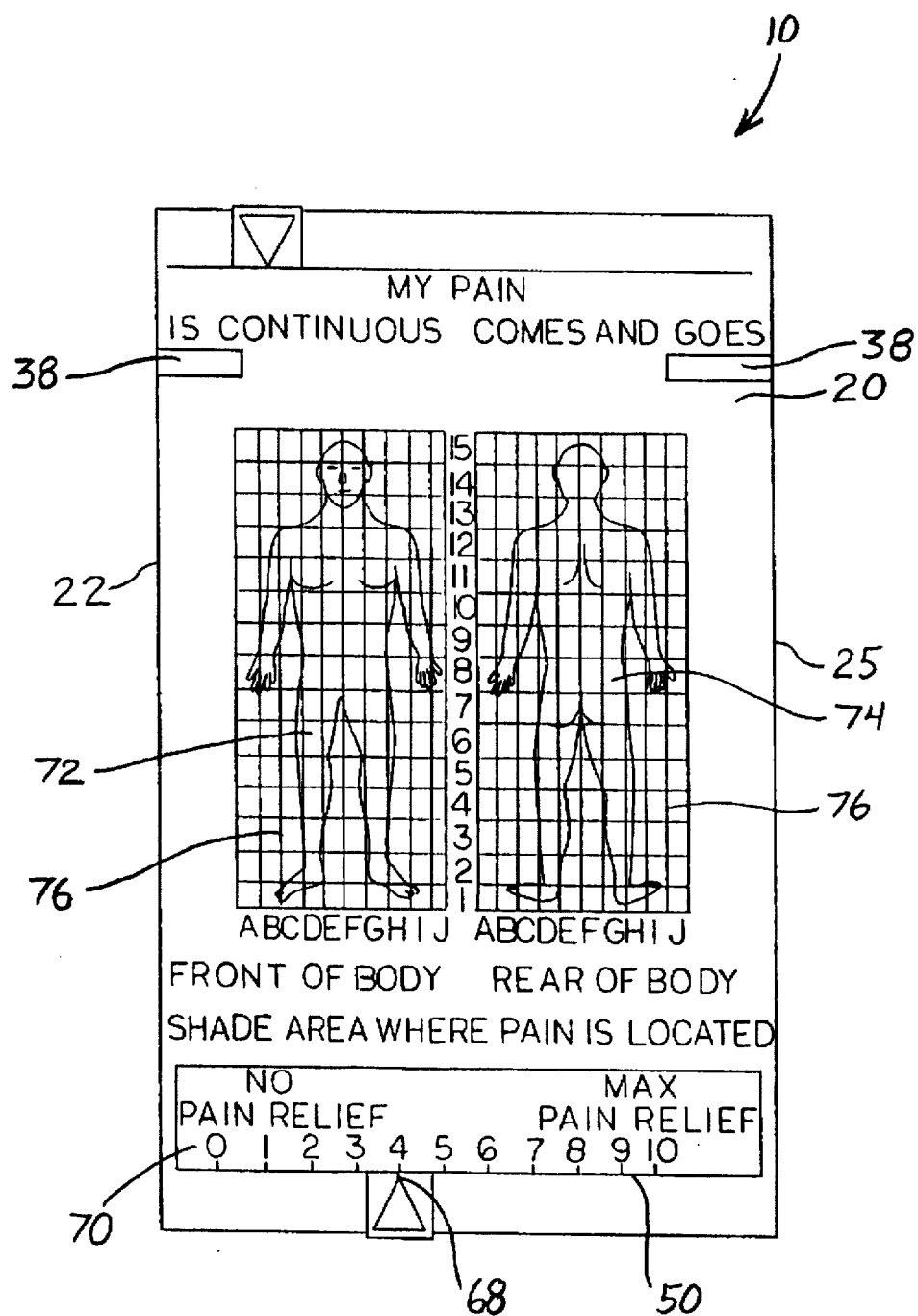
FIG. 3 is a bottom plan view of the pain measurement and recording tool.

FIG. 3 illustrates a second set of two selection indicator tabs 38 on bottom panel 20 for indicating variations in the continuity of pain. Under the words "my pain" is a left descriptor stating "is continuous" and a right descriptor stating "comes and goes". The user can indicate which descriptor applies to his or her pain by pivotally raising the associated tab 38.

A further cognitive dimension of the intensity of a person's pain is provided by an elongated first pain scale 40 which is displayed on top panel 18 in the illustrated embodiment adjacent a slidable scale indicator 42. The elongated first pain scale 40 includes a numbered scale ranging from zero to ten with the words "no pain" at the "zero" end of the scale and the words "worst possible pain" at the "ten" end of the scale. The first scale indicator 42 is slidably adjustable on base 12 between positions indicative of opposite extremes of the intensity of pain at the respective opposite ends of the scale 40 or the relative degree of intensity of pain corresponding to any position between the opposite ends of scale 40. In the illustrated embodiment, the first scale indicator 42 has an arrowhead 44 displayed thereon with an apex 46 at the top which is alignable with the zero and ten when the first scale indicator 42 is moved to the left and right limit positions respectively. To indicate the intensity of pain a person is experiencing, he or she need only adjust the first scale indicator 42 longitudinally along first pain scale 40 to the position where the arrowhead 44 corresponds to the intensity of pain being experienced by the person.

Figure 5:
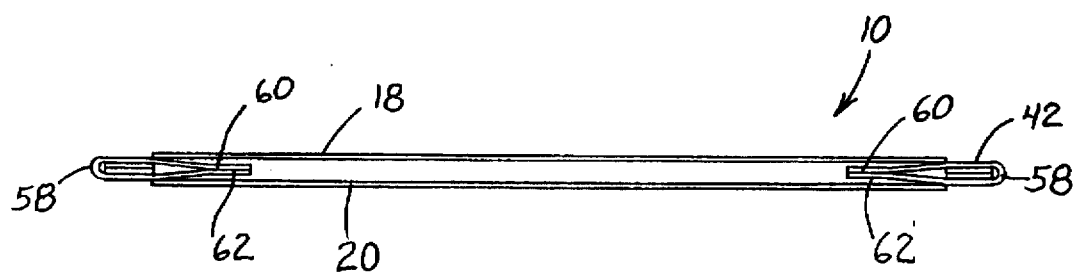
FIG. 5 is a side sectional view of the tool, as seen on line 5—5 in FIG. 2.

The construction of the first pain scale 40 in the illustrated embodiment is as follows. FIG. 6 illustrates that the front and back panels 18 and 20 have aligned slits 48 and 50 therethrough defining partially severed strips 52 and 54 adjacent the bottom edge 56 of base 12. The first elongated pain scale 40 is arranged along slit 18. The first scale indicator 42 encompasses both strips 52 and 54 and is slidable along them. Each strip 52 and 54 is connected at both of its ends to its respective front or back panel at the ends of the respective slit 48 or 50 defining that strip. The first scale indicator 42 is shown in FIG. 5 as a folded slide member having a folded edge 58 disposed adjacent the bottom edge 56 of base 12 and opposite free ends 60 and 62 joined together and situated between front and back panels 18 and 20 above the aligned slits 48 and 50. The free ends of the scale indicator may be joined together by adhesive or any other suitable means.

Figure 2:
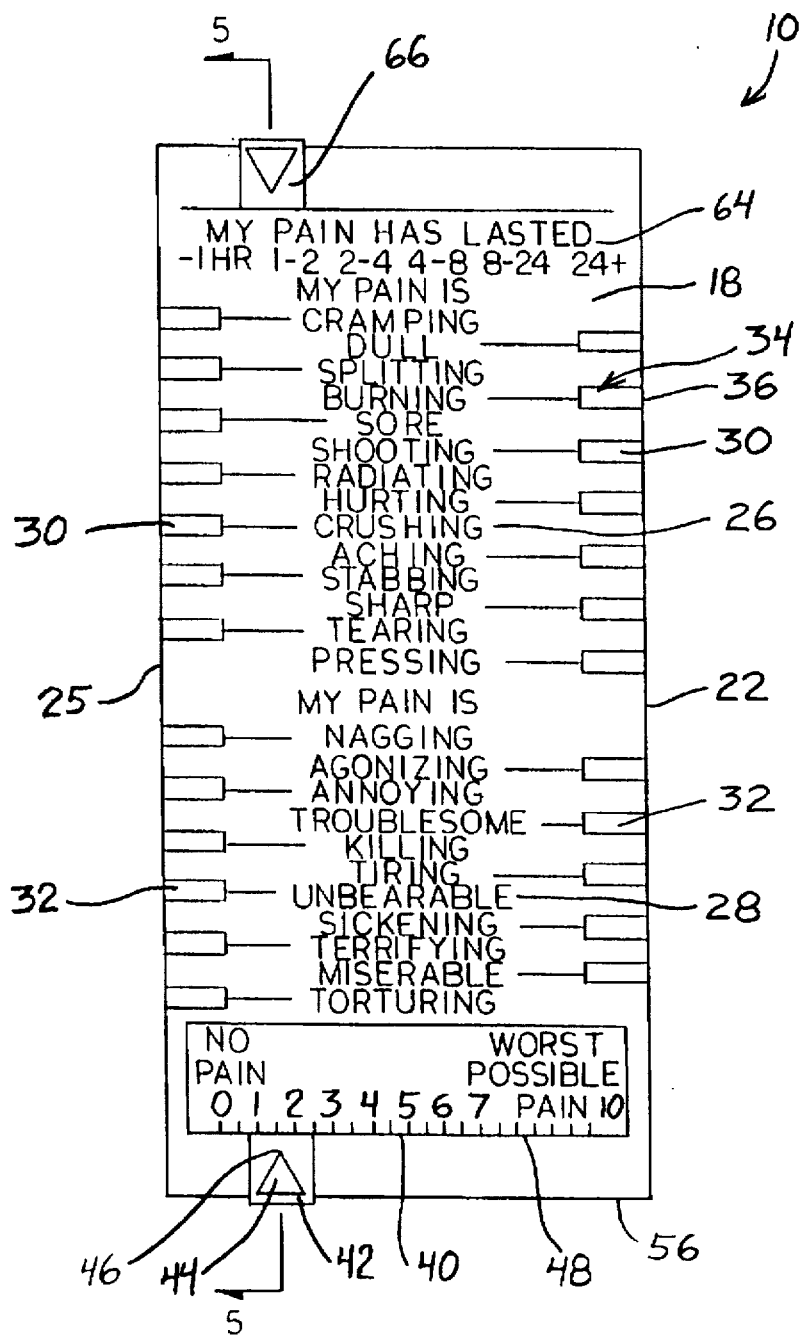
FIG. 2 is a top plan view of the pain measurement and recording tool.

FIG. 2 shows a second elongated scale 64 at the top of front panel 18, which scale is indicative of variations of pain duration. A second scale indicator 66 is slidably adjusted on base 12 between positions indicative of short duration at the left end of the scale and long duration at the other end of the scale or the relative extent of duration corresponding to any position therebetween. In the illustrated example of FIG. 2, the scale includes the words "My pain has lasted" above a numbered scale ranging from one hour at the left end to twenty-four hours at the right end, with the following ranges indicated therebetween, "1-2 2-4 4-8 8-24". The construction of second scale indicator 66 and the associated slits 48 and 50 and end strips 52 and 54 are identical to the similar structure at the opposite end of the base 12 for first scale indicator 42.

Referring to FIG. 3, the back side of the first scale indicator 42 displays an arrowhead 68 which serves as a third scale indicator in association with a third elongated pain scale 70 indicative of variations of pain relief. The third scale indicator is slidable on base 12 between positions indicative of no pain relief at one end of third scale 70 and maximum pain relief at the other end or the relative extent of pain relief corresponding to any position therebetween. In the illustrated example, third pain scale 70 includes a numbered scale ranging from zero to ten with the caption "no pain relief" corresponding to the zero position and the caption "max pain relief" corresponding to the "ten" position.

In an alternate embodiment, the third pain scale for indicating variations of pain relief may be situated along the top edge of back panel 20 so that the scale at the bottom of the back panel could include the numbered scale corresponding to the first pain scale for intensity. Thus a user looking at the first pain scale at the bottom of front panel 18 would not be influenced by the numbered scale when selecting the appropriate position of first scale indicator 42. The numbered scale would then still be available on the back panel to provide a numerical setting that could be recorded as a quantitative measurement of the cognitive indication of pain intensity set by a person viewing the first pain scale on front panel 18.

Referring to FIG. 3, back panel 20 displays separate illustrations of a human body, a left illustration 72 of the front of a body and a right illustration 74 of the back of a human body. In order to identify a location on illustrations 72 and 74 corresponding to the location of pain on a person, a respective grid 76 overlies each illustration. Two scales are associated with each grid for identifying a top to bottom and side to side position on the grid and respective illustration. In the illustrated example, a vertical numerical scale ranges from one to fifteen and the horizontal scale for each grid ranges from A to J. Thus a pain in the front portion of a person's right shoulder could be identified by shading in the box corresponding to position C-12 in the left hand illustration. Similarly, any other position on the body can be indicated by a person by shading the area of pain on one or the other illustration, which location can be transferred to a recording document by the numerical and alphabetical coordinates of the shaded area.

In operation, a multidimensional indication of the pain being experienced by a person can be obtained by providing the tool 10 of the invention to a person and causing him or her to adjust the first selection indicators 30 and 32 to the positions indicating whether or not the associated sensory and emotional descriptors 26 and 28 are descriptive of the person's pain.

Likewise, the person is requested to adjust the second selection indicators 38 on back panel 20 to positions indicating whether their pain is "continuous" or "comes and goes"0 to provide an indication of the continuity dimension of their pain.

The person is then requested to slidably adjust first scale indicator 42 along first pain scale 40 at the bottom of the front panel to provide an indication of the intensity dimension of their pain. Similarly, the second scale indicator 66 is slidably adjusted along second scale 64 at the top of front panel 18 to provide an indication of the duration dimension of their pain. The person can then shade in those portions of the human body illustrations 72 and 74 on back panel 20 which indicate the location of pain experienced by the person. For later use, after pain medication or treatment has been administered, the pain relief scale 70 on the back panel 20 may be used to provide a quantitative measurement of the pain relief experienced by the person as a result of that medication or treatment.

To quantify the recorded pain for record keeping or comparison of the pain recorded at different times, quantitative measurements of the various dimensions of the pain are readily available by simply observing the positions of the first selection indicators 30, 32, second selection indicators 38 and various scale indicators. A quantitative measurement of the sensory and emotional dimensions of the pain are obtained by adding up the ranks of the pain descriptors adjacent those selection indicators adjusted by the person to the first state, indicating that those descriptors are accurately descriptive of the patient3 s pain. The ranks of the selected sensory pain descriptors are added up separately from the ranks of the selected emotional pain descriptors as indicated in the following example.

EXAMPLE

Person Chooses the Following Descriptors:

| Sensory Descriptors | Rank | Emotional Descriptors | Rank |
|---|---|---|---|
| Sharp | 5 | Agonizing | 4 |
| Aching | 3 | Troublesome | 2 |
| Burning | 4 | Annoying | 1 |
|  | 12 | Nagging | 1 |
|  |  |  | 8 |

Pain Intensity Scores

| Sensory | 12 |
|---|---|
| Emotional | 8 |
| Total | 20 |

The above is one example of how scores are calculated and analyzed on the instrument of the invention. In this example, the sensory pain is more intense than the emotional pain. Accordingly, a physician would choose a treatment or medication that would be directed at reducing the sensory component of pain. For a woman experiencing labor pain, for example, the physician's choice of medication might be epidural anesthesia rather than valium, a drug directed at reducing the emotional component of pain. In comparison, a patient who has cancer may choose fewer and less intense sensory words than emotional words to represent the treatment would be directed at reducing the emotional component of a pin, i.e., staying with the patient, giving information about what to expect, relaxation exercises, self-coping statements, tranquilizers, etc.

A quantitative reading of the intensity dimension of pain can be observed and recorded from the first scale 40 at the bottom of the front panel. A quantitative measurement of the duration dimension of pain can be observed and recorded from the second pain scale 64 at the top of front panel 18. A quantitative measurement of the pain relief dimension can be observed and recorded from the position of the scale indicator at the bottom of the back panel 20.

Finally, a quantitative measurement of the location dimension of one's pain can be observed and recorded from the human body illustrations 72 and 74 on back panel 20 by recording the alphabetic and numeric coordinates of the shaded areas of each illustration.

This instrument will be useful in hospitals, doctors offices, nursing homes and even in a home medicine cabinet where a person could use the instrument to effectively communicate his or her pain by telephone to a physician or other medical personnel. It has been found that reliable readings are obtainable from anyone over the age of 8 or 9.

Whereas the invention has been shown and described in connection with a one embodiment thereof, it is apparent that many modifications, substitutions and additions may be made which are within the intended broad scope of the appended claims. For example, the material of the base 12 could be cardboard sheet material for an inexpensive tool intended for limited use. Laminated sheet material may be used for a more durable tool or a rigid plastic for a permanent tool designed for repetitive use over a long period of time.

The size of the tool is preferably selected so that the various scales are ten centimeters long. To minimize the overall size of the tool, it may be preferred to arrange the pain scales along the long edges of the tool rather than the short edges. A small tool could be provided to carry in one's pocket or wallet. A larger tool may be required for older patients to be sure that all scales are large enough to be easily read. The range of pain covered by any given scale need not be physical extremes but rather may be any selected range such as that indicated for duration on the second pain scale with the extremes being the limits of the selected range. The human body illustrations on back panel 20 may be presented on a high gloss surface which can be marked with an erasable marker and then wiped clean for subsequent use. Likewise, the scales could be changed to provide alphabetic characters along the vertical axis and numbers on the horizontal axis along the grids for both illustrations.

The instrument is not only useful for communicating pain in the first encounter with a physician, but may also be used for choosing medication and determining the effect of the medication. Furthermore, the instrument is useful for measuring the efficacy of lowering pain by various treatments such as medication, acupuncture, hypnosis, analgesia and bio feedback among others.

Thus there has been shown and described an apparatus and method for providing a multidimensional indication of a pin, which apparatus and method accomplish at least all of the stated objects.

I claim:

1. A tool for providing a multidimensional indication of the pain being experienced by a person, comprising,
   a base,
   a plurality of pain descriptors displayed on said base, said pain descriptors being indicative of variations of a first dimension of pain selected from the group consisting of nature, intensity, location, duration, continuity, and pain relief,
   a selection indicator operatively associated with each descriptor, each selection indicator being on said base and selectively adjustable by a person between a first state indicating that the associated descriptor describes the person's pain and a second state indicating that the associated descriptor does not describe the person's pain,
   a first elongated scale indicative of variations of a second dimension of pain selected from the above mentioned group,
   a first scale indicator slidably supported on said base in association with said scale, said first scale indicator being slidably adjustable on said base between positions indicative of opposite extremes of said second dimension of pain at respective opposite ends of said first scale or the relative degree of said second dimension of pain corresponding to any position between said opposite ends, thereby to provide a cognitive measurement of the second dimension of pain,
   a second elongated scale indicative of variations of a third dimension of pain selected from the above mentioned group, and
   a second scale indicator slidably supported on said base in association with said second scale, said second scale indicator being slidably adjustable on said base between positions indicative of opposite extremes of said third dimension of pain at respective opposite ends of said second scale or the relative degree of said third dimension corresponding to any position between said opposite ends of the second scale, thereby to provide a cognitive measurement of the third dimension of pain.

2. A tool for providing a multidimensional indication of the pain being experienced by a person, comprising,
   a base,
   a plurality of pain descriptors displayed on said base, said pain descriptors being indicative of variations of a first dimension of pain selected from the group consisting of nature and continuity,
   a selection indicator operatively associated with each descriptor, each selection indicator being on said base and selectively adjustable by a person between a first state indicating that the associated descriptor describes the person's pain and a second state indicating that the associated descriptor does not describe the person's pain,
   a first elongated scale indicative of variations of a second dimension of pain selected from a second group consisting of intensity, duration and pain relief,
   a first scale indicator slidably supported on said base in association with said scale, said first scale indicator being slidably adjustable on said base between positions indicative of opposite extremes of said second dimension of pain at respective opposite ends of said first scale or the relative degree of said second dimension of pain corresponding to any position between said opposite ends, thereby to provide a cognitive measurement of the second dimension of pain,
   a second elongated scale indicative of variations of a third dimension of pain selected from said second group, and
   a second scale indicator slidably supported on said base in association with said second scale, said second scale indicator being slidably adjustable on said base between positions indicative of opposite extremes of said third dimension of pain at respective opposite ends of said second scale or the relative degree of said third dimension corresponding to any position between said opposite ends of the second scale, thereby to provide a cognitive measurement of the third dimension of pain.

3. The tool of claim 2 wherein said plurality of pain descriptors are indicative of variations in the nature of pain and include a plurality of verbal pain descriptions.

4. The tool of claim 3 wherein said verbal pain descriptions comprise sensory pain descriptions and include a plurality of adjectives describing sensory aspects of pain.

5. The tool of claim 4 wherein said verbal pain descriptions further comprises emotional pain descriptions and include a plurality of adjectives indicative of emotional aspects of pain.

6. The tool of claim 2 wherein said first elongated scale is indicative of variations of pain intensity, said first scale indicator being slidably adjustable on said base between positions indicative of worse possible pain at one end of said first scale and no pain at the other end of the first scale or the relative extent of pain corresponding to any position therebetween.

7. The tool of claim 2 wherein said second elongated scale is indicative of variations of pain duration, said second scale indicator being slidably adjustable on said base between positions indicative of short duration at one end of said second scale and long duration at the other end of said second scale or the relative extent of duration corresponding to any position therebetween.

8. The tool of claim 2 wherein said second elongated scale is indicative of variations of pain relief, said second scale indicator being slidably adjustable on said base between positions indicative of no pain relief at one end of said scale and maximum pain relief at the other end of said scale or the relative extent of pain relief corresponding to any position therebetween.

9. The tool of claim 2 wherein said plurality of pain descriptors are indicative of variations in the continuity of pain and include a plurality of verbal descriptions of continuity.

10. The tool of claim 9 wherein said verbal descriptions of continuity include a plurality of words describing relative degrees of continuity.

11. The tool of claim 2 further comprising an illustration of a human body and means for identifying a location on said illustration corresponding to the location of pain on the person.

12. The tool of claim 11 wherein said illustration of a human body includes separate illustrations of a front and back of a human body.

13. The tool of claim 11 wherein said means for identifying a location on said illustration includes a grid overlying said illustration, and two scales associated with said grid for identifying a top to bottom and side to side position on said grid and illustration.

14. The tool of claim 13 wherein said two scales are arranged along perpendicular horizontal and vertical axis relative to said grid.

15. The tool of claim 2 wherein said base comprises a folded sheet including a front panel and back panel, said front and back panels having aligned slits therethrough defining partially severed strips adjacent one edge of said base, said first elongated scale being arranged along said slits and said first scale indicator encompassing said strips and being slidable thereon.

16. The tool of claim 15 wherein each strip is connected at both of its ends to its respective panel at the ends of the slit defining that strip.

17. The tool of claim 16 wherein said first scale indicator comprises a folded slide member having a folded edge disposed adjacent the edge of said base and opposite ends joined together between said front and back panels.

18. The tool of claim 15 wherein said selection indicator comprises a pivotal tab formed in a respective panel and having one end pivotally connected to said panel so that said tab is selectively adjustable between a substantially intact position and a pivotally raised position engaging said panel only at said one end of the tab.

19. A tool for providing a multidimensional indication of the pain being experienced by a person, comprising, a base, a first elongated scale on said base, said first scale indicative of variations of a first dimension of pain selected from the group consisting of intensity, duration, and pain relief, a first scale indicator slidably supported on said base in association with said scale, said first scale indicator being slidably adjustable on said base between positions indicative of opposite extremes of said first dimension of pain at respective opposite ends of said first scale, or the relative degree of said first dimension of pain corresponding to any position between said opposite ends, thereby to provide a cognitive measurement of the first dimension of pain, a second elongated scale on said base, said second scale indicative of variations of a second dimension of pain selected from the above mentioned group, and a second scale indicator slidably supported on said base in association with said second scale, said second scale indicator being slidably adjustable on said base between positions indicative of opposite extremes of said second dimension of pain at respective opposite ends of said second scale or the relative degree of said second dimension corresponding to any position between said opposite ends of said second scale, thereby to provide a cognitive measurement of the second dimension of pain.

20. The tool of claim 19 further comprising a third elongated scale on said base, said third scale indicative of variations of a third dimension of pain selected from the aforementioned group, and a third scale indicator slidably supported on said base in association with said third scale, said third scale indicator being slidably adjustable on said base between positions indicative of opposite extremes of said third dimension of pain at respective opposite ends of said third scale or the relative degree of said third dimension corresponding to any position between said opposite ends of the third scale, thereby to provide a cognitive measurement of the third dimension of pain.

21. The tool of claim 19 wherein said base includes opposite front and back surfaces, said first and second scales being similarly arranged on respective opposite surfaces of said base, said first and second scale indicators comprising opposite front and back surfaces of a single unitary indicator slidably supported on said base in association with said first and second scales.

22. The tool of claim 20 wherein said first elongated scale is indicative of variations of pain intensity, said first scale indicator being slidably adjustable on said base between positions indicative of worse possible pain at one end of said first scale and no pain at the other end of the first scale or the relative extent of pain corresponding to any position therebetween.

23. The tool of claim 22 wherein said second elongated scale is indicative of variations of pain duration, said second scale indicator being slidably adjustable on said base between positions indicative of short duration at one end of said second scale and long duration at the other end of said second scale, or the relative extent of duration corresponding to any position therebetween.

24. The tool of claim 23 wherein said third elongated scale is indicative of variations of pain relief, said third scale indicator being slidably adjustable on said base between positions indicative of no pain relief at one end of said third scale and maximum possible pain relief at the other end of said third scale or the relative extent of pain relief corresponding to any position therebetween.

25. A tool for providing a multidimensional indication of the pain being experienced by a person, comprising, a base having front and back surfaces, a plurality of first pain descriptors displayed on said base, said first pain descriptors being indicative of variations in the nature of pain and include a plurality of verbal pain descriptions, a plurality of first selection indicators, each operatively associated with a respective first pain descriptors and being mounted on said base and selectively adjustable by a person between a first state indicating that the respective pain descriptor describes the person's pain and a second state indicating that the associated pain descriptor does not describe the person's pain, a plurality of second pain descriptors displayed on said base, said second pain descriptors being indicative of variations in the continuity of pain and include a plurality of verbal descriptions of continuity, a plurality of second selection indicators, each operatively associated with a respective second pain descriptor and each being mounted on said base and selectively adjustable by a person between a first state indicating that the associated second pain descriptor describes the continuity of the person's pain and the second state indicating that the associated second pain descriptor does not describe the continuity of the person's pain, a first elongated scale indicative of variations of pain intensity, a first scale indicator slidably supported on said base and being slidably adjustable on said base between positions indicative of worse possible pain at one end of said first scale and no pain at the other end of the first scale, or the relative extent of pain corresponding to any position therebetween, a second elongated scale on said base, said second elongated scale being indicative of variations of pain duration, a second scale indicator slidably supported on said base in association with said second scale, said second scale indicator being slidably adjustable in said base between positions indicative of short duration at one end of said second scale and long duration at the other end of said second scale, or the relative extent of duration corresponding to any position therebetween, a third elongated scale on said base indicative of variations of pain relief, and a third scale indicator slidably supported on said base in association with said third scale, said third scale indicator being slidably adjustable on said base between positions indicative of no pain relief at one end of said scale and maximum pain relief at the other end of said scale or the relative extent of pain relief corresponding to any position therebetween.

26. a method for providing a multidimensional indication of pain being experienced by a person, comprising, providing a tool having a plurality of pain descriptors displayed therein, said pain descriptors being indicative of variations of a first dimension of pain selected from the group consisting of nature, and continuity, a selection indicator operatively associated with each descriptor and adjustable to first and second states indicating that the associated descriptor is descriptive and nondescriptive respectively, first and second elongated scales on said base indicative of variations of respective second and third dimensions of pain selected from a second group consisting of intensity, duration and pain relief, and first and second respective scale indicators slidably adjustable on said tool and operative in association with said respective first and second scales to provide cognitive measurements of said respective second and third dimensions of pain, causing a person to adjust said selection indicators to said first and second states as s indications of whether the associated descriptors are descriptive of the pain being experienced by the person, causing a person to slidably adjust the first and second scale indicators to positions on said respective first and second pain scales indicative of the extent of said respective second and third dimensions of pain being experienced by the person, and observing the extent of said second and third dimensions of pain indicated by the adjusted first and second scale indicators on said respective first and second scales.

27. The method of claim 26 wherein said tool is a handheld tool and further comprising handing said tool to the person.

28. A method for providing a multidimensional indication of pain being experienced by a person, comprising, providing a tool having first and second elongated pain scales indicative of variations of respective first and second dimensions of pain selected from the group consisting of intensity, duration, and pain relief, and the first and second scale indicators slidably adjustable on said tool and operative in association with said respective first and second scales to provide a cognitive measurement of said first and second dimensions of pain, causing a person to slidably adjust the first and second scale indicators to respective positions on said first and second pain scales indicative of the extent of said respective first and second dimensions of pain being experienced by the person, and observing the cognitive measurement of said first and second dimensions of pain indicated by the respective adjusted first and second scale indicators on said respective first and second scales.

29. The method of claim 28 wherein said tool has a third elongated scale indicative of variations of a third dimension of pains selected from the aforementioned group and the third scale indicator slidably adjustable on said tool and operative in association with its said third scale to provide a cognitive measurement of said third dimension of pain, causing a person to slidably adjust the third scale indicator to a position on said third pain scale indicative of the extent of said third dimension of pain being experienced by the person, and observing the cognitive measurement of said third dimension of pain indicated by the adjusted third scale indicator on said third scale.

30. The method of claim 29 wherein said tool is a handheld tool and further comprising handing said tool to the person.

* * * * *